United States Patent
Flipo

(10) Patent No.: US 7,087,070 B2
(45) Date of Patent: Aug. 8, 2006

(54) MULTIPURPOSE CLAMP FOR MEDICAL USE COMPRISING TWO ARTICULATED JAWS

(76) Inventor: Bernard Flipo, 51 Avenue du Cap de Croix, Nice (FR) F-06100

(*) Notice: Subject to any disclaimer, the term of this patent is extended or adjusted under 35 U.S.C. 154(b) by 564 days.

(21) Appl. No.: 10/332,141

(22) PCT Filed: Jul. 2, 2001

(86) PCT No.: PCT/FR01/02106

§ 371 (c)(1),
(2), (4) Date: Jan. 6, 2003

(87) PCT Pub. No.: WO02/02019

PCT Pub. Date: Jan. 10, 2002

(65) Prior Publication Data

US 2003/0144693 A1 Jul. 31, 2003

(30) Foreign Application Priority Data

Jul. 5, 2000 (FR) .................................. 00 08858

(51) Int. Cl.
*A61B 17/28* (2006.01)
(52) U.S. Cl. ...................................... 606/205; 606/207
(58) Field of Classification Search ................ 606/205, 606/207, 208, 83, 184, 151, 116, 142; 30/122, 30/192; 81/427, 300, 360, 366; 72/409.01–409.19; 294/104, 118; 600/564
See application file for complete search history.

(56) References Cited

U.S. PATENT DOCUMENTS

| 1,462,202 A | 7/1923 | Hopper |
| 2,566,626 A | 9/1951 | Otto |
| 2,994,321 A * | 8/1961 | Tischler .................... 600/564 |
| 3,209,753 A * | 10/1965 | Hawkins et al. ............ 606/207 |
| 3,404,677 A | 10/1968 | Springer |
| 4,597,385 A | 7/1986 | Watson |
| 5,052,402 A | 10/1991 | Bencini et al. |
| 5,172,700 A * | 12/1992 | Bencini et al. ............. 600/564 |
| 5,217,460 A * | 6/1993 | Knoepfler ................... 606/52 |
| 5,507,296 A * | 4/1996 | Bales et al. ................. 600/564 |
| 5,667,526 A | 9/1997 | Levin |
| 5,693,069 A * | 12/1997 | Shallman ................... 606/205 |

FOREIGN PATENT DOCUMENTS

| DE | 30 23 671 | 1/1982 |
| DE | 90 05 519 | 7/1990 |
| DE | 94 13 527 | 1/1995 |
| DE | 298 10 758 | 10/1998 |

* cited by examiner

Primary Examiner—Anhtuan T. Nguyen
Assistant Examiner—Tuan V. Nguyen
(74) Attorney, Agent, or Firm—Young & Thompson

(57) ABSTRACT

A multifunction clamp for medical use includes two jaws articulated by a pivot and controlled by the practitioner from a gripping region. Each jaw (7, 8) includes, on its internal surface, a recess such that the two recesses form a hollow when the jaws (7, 8) are together, and each jaw (7, 8) has on its internal surface, at least one series of transverse striations, the series of striations being complementary to interfit when the jaws (7, 8) are together. Each jaw (7, 8) has at least one claw at its distal end, oriented toward the other jaw (7, 8).

17 Claims, 3 Drawing Sheets

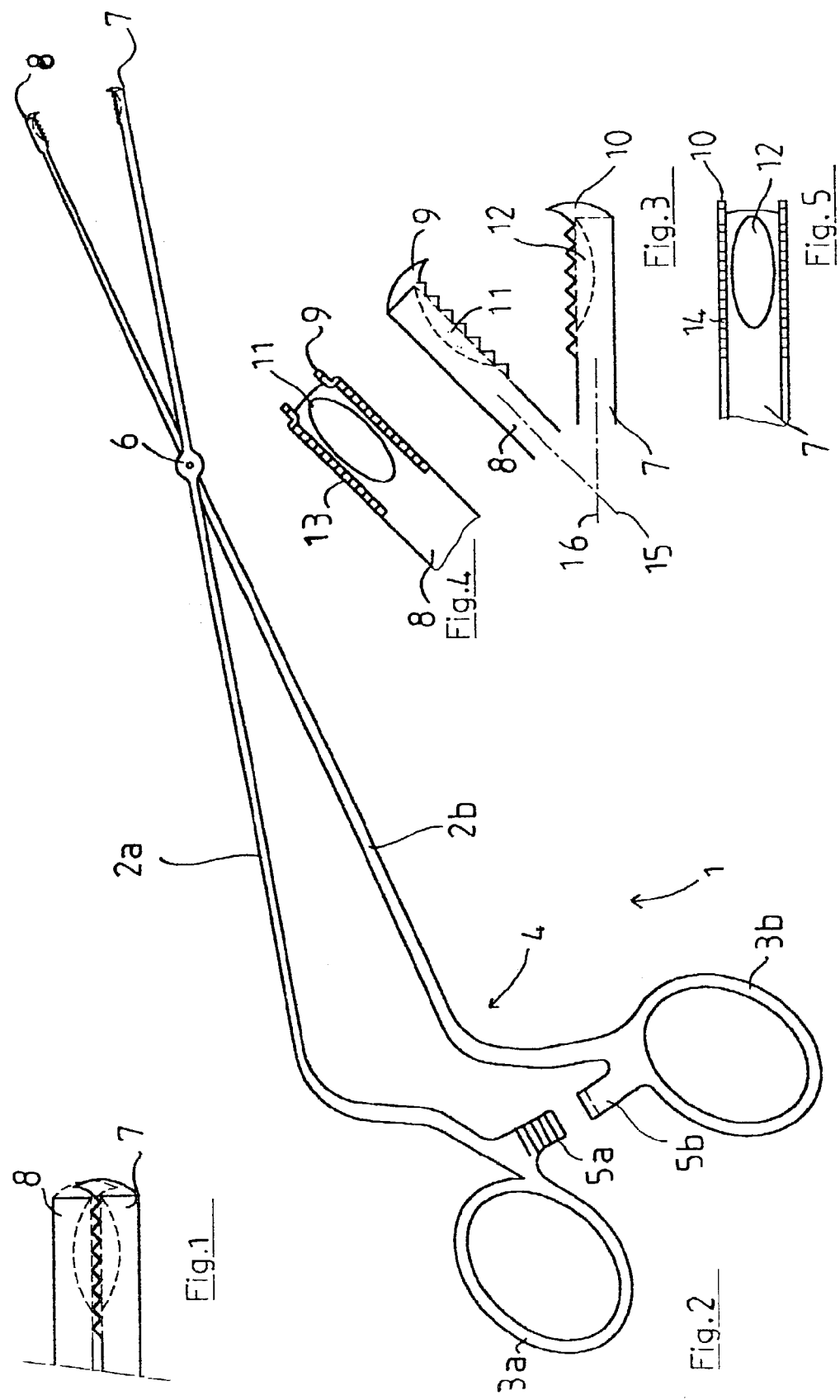

MULTIPURPOSE CLAMP FOR MEDICAL USE COMPRISING TWO ARTICULATED JAWS

BACKGROUND OF THE INVENTION

The present invention relates to a multifunctional clamp for medical use.

It finds application in the field of use and production of clamps for medical use particularly in the gynecological field.

DESCRIPTION OF THE RELATED ART

Clamps are commonly provided with two jaws articulated by a pivot and controlled by the practitioner from a gripping region.

In the gynecological field, particularly, there are conventionally used different clamps each fulfilling a specific function. Thus, there are known cotton carrying clamps, whose jaws have internal surfaces substantially flat, and provided with transverse parallel striations so as to permit gripping certain accessories, cotton, or else bandages.

There are also frequently used clamps called neck gripping.

In a way generally identical to the clamps described above, the neck gripping clamps comprise jaws provided with several claws at their end.

One can, with this claw, hold and/or remove the tissues such as those at the neck of the uterus.

Clamps particularly known in this regard are called MUSEUX clamps and POZZI clamps.

There are also commonly used in the gynecological field polyp clamps.

The internal surface of their jaws is excavated forming a reception member like a spoon.

By means of these cavities, it is possible to remove different elements and particularly polyps.

U.S. Pat. No. 5,667,526 discloses a clamp of a very particular shape provided with teeth that are quite prominent. It is usable only for certain limited functions and its complex action renders impossible its low cost production.

There is also known from U.S. Pat. No. 4,597,385 a biopsy clamp provided with a cutting member at the front of one of the jaws and two retention teeth for tissues. This clamp is also of limited interest because it is applicable only to carrying out biopsies. Its shape is also complicated because of the design of the jaws.

These different clamps give individual satisfaction in a general manner.

However, it has been discovered that it is necessary, for each patient, to have recourse to these three clamps in a cumulative manner.

The practitioner is thus obliged to have multiple sets of these different clamps for various successive patients.

In addition to the cost of purchase, such an arrangement imposes substantial costs of sterilization of the clamps.

A sterilization step of the clamps is routine after their use.

However, sterilization installations are generally costly, above all when they are dedicated for individual use of a practitioner in general practice.

Moreover, the sterilization must be carried out by someone having suitable competence, which also gives rise to a substantial cost in terms of labor.

Sterilizations, although very effective, do not always overcome the risk of failure of the obtained sterilization.

There is thus a great need to provide clamps permitting limiting the set of clamps necessary to gynecologists and preferably to avoid recourse to sterilization.

SUMMARY OF THE INVENTION

The present invention relates to this field and permits overcoming the drawbacks of clamps at present on the market.

One of the principal objects of the invention is to provide a clamp carrying out several functions from those performed at present by separate clamps.

In this sense, the present clamp has the advantage of fulfilling simultaneously the functions of a cotton carrying clamp, a neck gripping clamp and a polyp clamp.

Moreover, the fact of reducing the number of clamps permits making them disposable.

In this regard, the clamp according to the invention can be produced at least cost because of its design and its configuration and, if desired, of plastic material.

As a result, the invention associates the practical character of use of a single clamp, with the economic aspect of disposable instruments requiring no multiple sterilizations.

Another advantage of the invention is to provide a multifunctional clamp whilst maintaining its full and complete effectiveness for the carrying out of each of its functions, without the loss of time involved in conventional clamps that are not disposable.

According to a preferred modification, the clamp comprises incurved legs so as to exert a supplemental force on the jaws, after their contact, by resilient deformation of the legs. The forcible pressure is thus greatly promoted.

Other objects and advantages will become apparent from the description which follows, which is however not limiting of the invention.

The present invention relates to a multifunctional clamp for medical use comprising two jaws articulated by a pivot and controlled by the practitioner from a gripping region, characterized by the fact that:

each jaw comprises, on its internal surface, a recess such that the two recesses form a hollow when the jaws are together, each jaw comprises, on its internal surface, at least one series of transverse striations, said series of striations being complementary to interfit when the jaws are together, each jaw comprises at least one claw at its distal end, oriented toward the other jaw.

This clamp can be made according to various modifications introduced hereafter:

the recesses have symmetrical openings whose edges are in contact when the jaws are together, to create a closed hollow if desired with forcible pressure, the recesses have an elliptical shape whose major axis is oriented along the longitudinal axis of the jaw, each jaw comprises two series of striations formed on opposite sides of the recess along the direction of the longitudinal axis of the jaw, each jaw comprises two claws, the claws of the jaws interfitting in the closed position, the recesses extend to the distal end of the jaws between the two claws, the gripping region is formed by two legs with rings connected by a pivot for the jaws, said jaws being each formed in prolongation of a leg on the side of the pivot opposite the gripping region, the posterior region of the legs, located on the side of the pivot opposite the gripping region, is incurved convexly and is of material that is resiliently deformable during pressure of the jaws, the curvature of the two posterior portions is symmetrical, the forward portion of the legs, located on the same side of the pivot as the gripping region, is incurved in a convex manner and is of material that is resiliently deformable during pressure of the jaws, the curvature of the two front portions is symmetrical, the distance between the distal end of the jaws and the pivot is 7 to 9 cm, it is made of plastic material.

BRIEF DESCRIPTION OF THE DRAWINGS

The accompanying drawings are given by way of indicative example and are not limiting. They show one embodiment. They permit easy comprehension of the invention.

FIG. 1 is a fragmentary side view of the end of a clamp in a particular embodiment of the invention.

FIG. 2 is an overall view of one embodiment of the multifunctional clamp shown here.

FIG. 3 is a fragmentary side view of the jaws of a clamp in the open position.

FIG. 4 is view from below of one of the jaws of the clamp according to the invention.

FIG. 5 is a view from above of the other jaw according to a possible embodiment.

DESCRIPTION OF THE PREFERRED EMBODIMENTS

Figure 6:
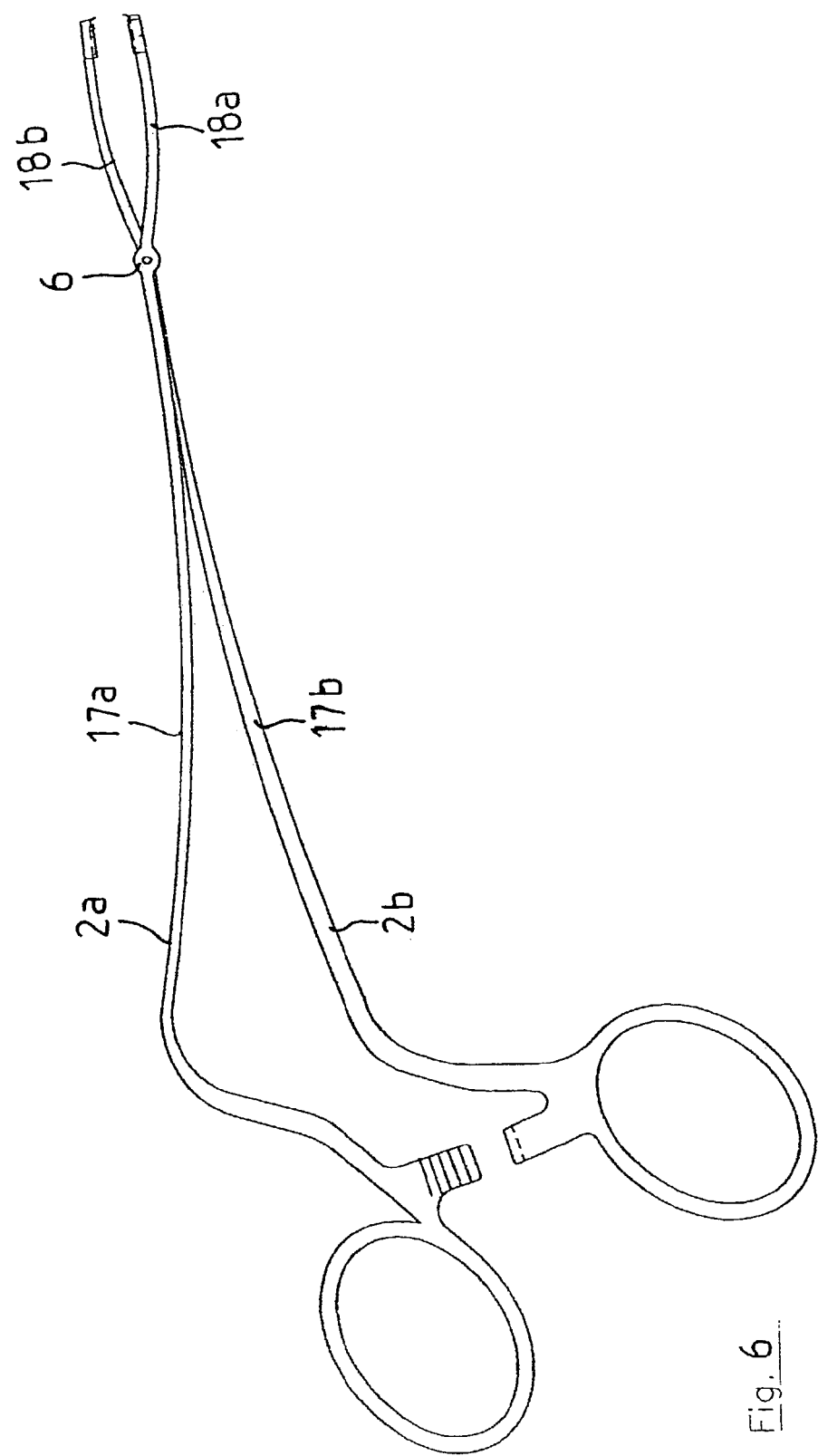
FIG. 6 shows a preferred arrangement of the legs of the clamp, the jaws being open.

FIG. 2 show a general view of an embodiment of the clamp disclosed here.

According to this preferred example, the clamp comprises a gripping region 1 substantially at one of its ends, formed by two elongated legs numbered 2a, 2b, and provided with rings at their ends, numbered 3a, 3b.

The rings permit gripping by the practitioner so as to control the opening and closing of the clamp.

In the illustrated embodiment, the legs 2a, 2b are connected by a pivot 6 known in the technical field in question at the present.

Moreover, as shown in FIG. 2, the jaws 7, 8 which comprise the clamp are each formed in prolongation of one of the legs 2a, 2b on the other side of the pivot 6 relative to the gripping region 1.

Referring to the relative arrangement of the jaws in FIG. 2, we will call the lower jaw the jaw 7 and the upper jaw the jaw 8.

Any other shape of clamp is of course envisagable according to the invention, and the particular arrangement of FIG. 2 is given only by way of example.

Similarly, the elbowed portion 4 of the legs 2a, 2b is not necessary, and a clamp could be envisaged whose two legs are substantially straight.

To permit the production of a multifunctional clamp, the jaws 7, 8 have specific means.

Thus, each jaw 7, 8 comprises on its internal surface a recess 11, 12 as shown respectively in FIGS. 4 and 5.

The formation of such recesses 11, 12 permits creating a hollow within the jaws 7, 8 when these latter are together, if desired forcibly.

By way of example, but preferably, the recesses 11, 8 have an elliptical shape whose major axis is oriented along the longitudinal axis of the jaw 7, 8.

A small spacing between the edge of the recess 11, 12 and the end of the jaw 7, 8 is desirable, for example 1 mm, to facilitate its use.

The length of the major axis of the recesses 11, 12 can be for example 15 mm.

Preferably, the recesses 11, 12 have similar shape and dimensions and are disposed symmetrically on the jaws 7 and 8 so as to face each other.

Thus, their symmetrical openings permit creating a closed hollow when the jaws are together, the edges of the openings of the recesses being in contact in this position.

The edge of the openings can in this case be at mid-height of the striations 13, 14 described hereafter.

The recesses 11, 12 thus formed permit removing tissues or else polyps.

The clamp shown here also permits gripping and manipulation of various accessories such as cotton, coils, . . .

It also provides a clamp which is commonly called a cotton carrying clamp.

To do this, each jaw 7, 8 comprises on its internal surface at least one series of striations numbered 13 and 14 in FIGS. 4 and 5.

As shown, these striations are transverse relative to the longitudinal axis 15, 16 of the jaws 7, 8.

Moreover, as can be seen from FIGS. 2 and 3, the striations 13, 14 disposed on each of the jaws 7, 8 are complementary so as to interfit when the jaws 7, 8 are together as in FIG. 1.

Preferably, there will be formed two series of striations 13, 14 on each jaw 7, 8.

More precisely, these two series of striations can be disposed on opposite sides of the recess 11, 12.

This arrangement can be clearly seen in FIGS. 4 and 5.

It will be noted that such an arrangement is particularly advantageous in terms of size.

Thus, the striations 13, 14 thus provided completely fulfill their functions of grasping the different accessories without at the same time occupying all the width of the internal surface of the jaws 7, 8.

Moreover, an arrangement of the series of striations substantially adjacent the lateral edges of the jaws 7, 8 ensures good gripping in position of the jaws 7, 8 even if they are twisted when together.

Moreover, it will be noted that the elliptical shape preferred for the recesses 11, 12 permits the formation of a hollow of a sufficient volume whilst preserving a lateral space for the formation of the series of striations 13, 14.

The clamp according to the invention also fulfills the function of a neck gripping clamp.

To this end, at least one claw 9, 10 is formed at the distal end of each jaw 7, 8.

In the example shown in the figures, there are provided two claws 9, 10 on each jaw 7, 8.

As can be seen in FIG. 3, the claws of each jaw 7, 8 are oriented toward the other jaw.

Moreover, when the jaws 7, 8 are together, the claws 9, 10 of the jaws 7, 8 are such that they interfit. In this way, they do not interfere with the closed position of the jaws 7, 8.

An example of embodiment of the claws 9, 10 interfitting is shown in FIG. 1.

For the convenience of the practitioner, the recesses 11, 12 extend preferably to the distal end of the jaws 7, 8 between the claws 9, 10. In this way, the hollow for the reception of a polyp is located adjacent the end of the clamp.

Again for the convenience of use and by way of example, the distance between the distal end of the jaws 7, 8 and the pivot 6 could be from 7 to 9 centimeters.

Moreover, there could be formed closure tongues 5a, 5b in the gripping region 1.

By these means, it is possible to hold the clamp in closed position with if desired a slight restraint for permanent closure.

Closure tongues 5a and 5b as shown in FIG. 2 and of the present design could also be used.

It will be seen from the description and the drawings that the clamp according to the invention fulfills several functions in a manner as effective as clamps individually provided to fulfill each of these functions.

Moreover, this creation is effected without having recourse to a complicated design which would increase the cost of production of the clamps.

Still further, the configuration of these clamps is such that they can be made of plastic material and for example, by molding.

In this way, there can be provided low cost clamps which are adapted for single use.

Particularly, for production in plastic material, it is important to preserve the optimum characteristics under pressure, when the jaws 7, 8 are closed.

To do this, it is preferably proposed to give an incurved shape to the legs 2a, 2b, permitting resilient deformation of the legs when the jaws are in contact, to increase the applied force.

There will be used a material whose properties of resilient deformation are in accordance with the degree of deformation desired for the legs 2a, 2b.

The curvature given to the legs 2a, 2b is the reverse of that which it has a tendency to adopt when the force is applied to jaws 7, 8.

Figure 7:
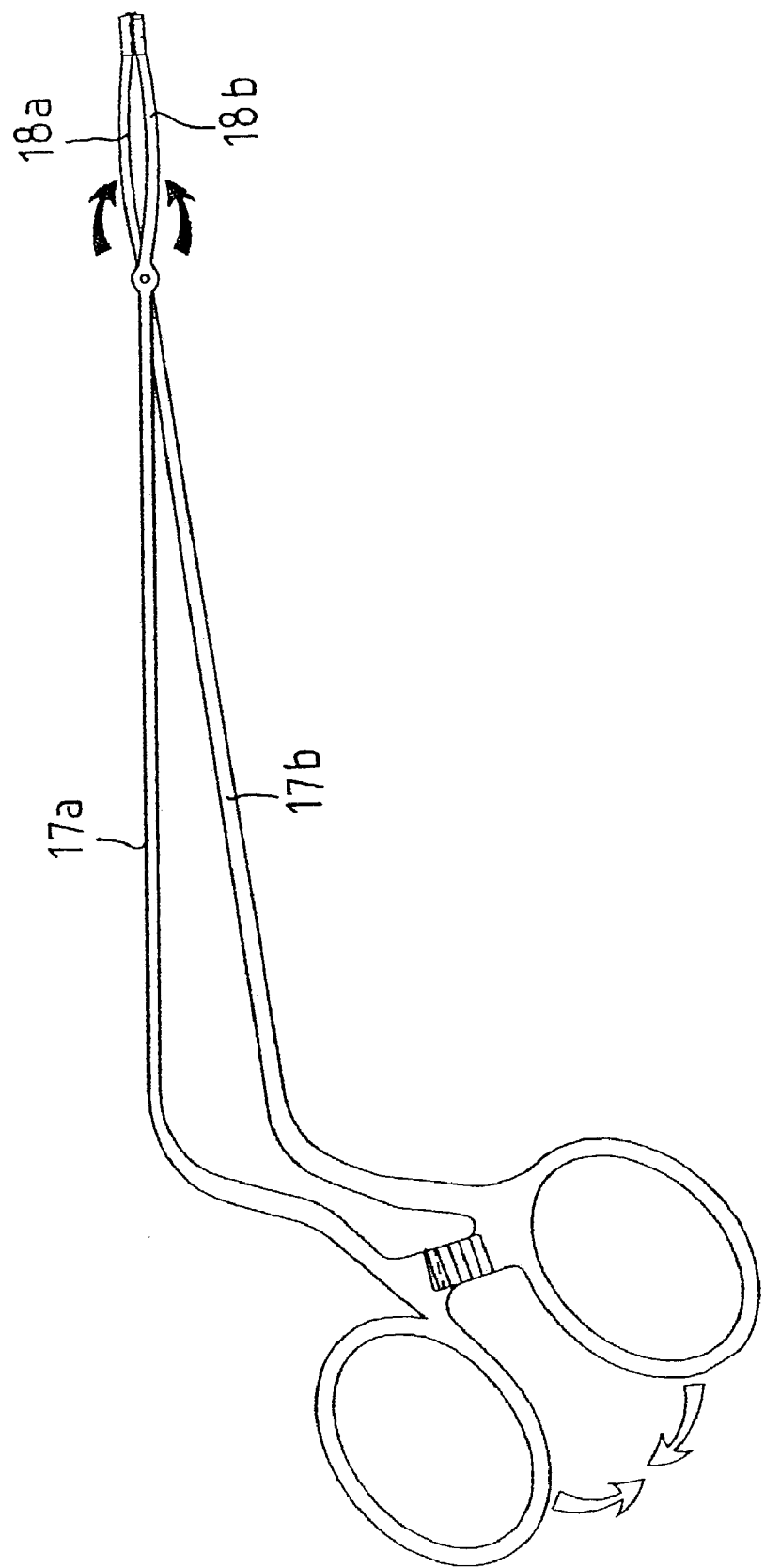
FIG. 7 is a view with closed jaws of another modified design of the clamp.

Referring to FIG. 7, there is seen the shape of the posterior portions 18a, 18b of the legs 2a, 2b (these portions are those located on the side opposite the gripping region 1) having a convex curvature, preferably symmetrically.

The black arrows in FIG. 7 show the direction of resilient deformation which has a tendency to overcome the convex curvature.

In a supplemental or alternative manner, the rear portions 17a, 17b of the legs 2a, 2b (these portions are on the same side as the gripping region 1) have a concave curvature, as shown in FIG. 6.

The production of such a clamp with curved legs as in FIGS. 6 and 7 is possible moreover with any type and design of jaws.

REFERENCES

1. Gripping region
2a, 2b—Legs
3a, 3b—Rings
4. Elbow
5a, 5b—Closure tongues
6. Pivot
7. Lower jaw
8. Upper jaw
9. Upper claws
10. Lower claws
11. Upper recess
12. Lower recess
13. Upper striations
14. Lower striations
15. Longitudinal axis of the upper jaw
16. Longitudinal axis of the lower jaw
17a, 17b. Rear portion
18a, 18b. Front portion

The invention claimed is:

1. Multifunctional clamp for medical use by a practitioner, comprising:
    a practitioner gripping region (1); and
    two jaws (7, 8) pivotally articulated and controlled by the practitioner from the gripping region (1),
    each jaw (7, 8) comprising, on an internal surface, a recess (11, 12) such that the two recesses (11, 12) form a hollow volume when the jaws (7, 8) are together,
    each jaw (7, 8) comprising, on the internal surface, two series of transverse striations (13, 14) formed on opposite sides of the recess (11, 12) in the direction of the longitudinal axis (15, 16) of the jaw (7, 8),
    said series of striations (13, 14) being complementary so as to interfit when the jaws (7, 8) are together,
    each jaw (7, 8) comprising at least two claws (9, 10) at a distal end of the jaw, each claw oriented toward another claw (9, 10) on another jaw and interfitting with the another claw in the closed position, and
    the recesses (11, 12) having symmetrical openings with edges that contact with each other when the jaws (7, 8) are together.

2. Multifunctional clamp according to claim 1, wherein, with the jaws (7, 8) together, the recesses create a closed hollow space.

3. Multifunctional clamp according to claim 2, wherein, the recesses (11, 12) have an elliptical shape with a major axis oriented along the longitudinal axis (15, 16) of the jaw (7, 8).

4. Multifunctional clamp according to claim 1, wherein, the recesses (11, 12) have an elliptical shape with a major axis oriented along the longitudinal axis (15, 16) of the jaw (7, 8).

5. Multifunctional clamp according to claim 1, wherein, the recesses (11, 12) extend to the distal end of the jaws (7, 8) and between the two claws (9, 10).

6. Multifunctional clamp according to claim 5, wherein, the gripping region (1) comprises two legs (2a, 2b) with rings (3a, 3b) connected by a pivot (6) forming the piVot of the jaws (7, 8),
    said jaws (7, 8) being each formed in the prolongation of one leg (2a, 2b) on the side of the pivot (6) opposite the gripping region (1).

7. Multifunctional clamp according to claim 1, wherein, the gripping region (1) comprises two legs (2a, 2b) with rings (3a, 3b) connected by a pivot (6) forming the pivot of the jaws (7, 8),
    said jaws (7, 8) being each formed in the prolongation of one leg (2a, 2b) on the side of the pivot (6) opposite the gripping region (1).

8. Multifunctional clamp according to claim 7, wherein, a front portion (18a, 18b) of the legs (2a, 2b), located on the side of the pivot (6) opposite the gripping region (1), is incurved convexly and is of a material that is resiliently deformable during pressure of the jaws (7, 8).

9. Multifunctional clamp according to claim 8, wherein, a rear portion (17a, 17b) of the legs (2a, 2b), located on the same side of the pivot (6) as the gripping region (1), is incurved in a concave manner and is of a material that is resiliently deformable during pressure of the jaws (7, 8).

10. Multifunctional clamp according to claim 8, wherein, the curvature of the two front portions (18*a*, 18*b*) is symmetrical.

11. Multifunctional clamp according to claim 10, wherein, a rear portion (17*a*, 17*b*) of the legs (2*a*, 2*b*), located on the same side of the pivot (6) as the gripping region (1), is incurved in a concave manner and is of a material that is resiliently deformable during pressure of the jaws (7, 8).

12. Multifunctional clamp according to claim 7, wherein, a rear portion (17*a*, 17*b*) of the legs (2*a*, 2*b*), located on the same side of the pivot (6) as the gripping region (1), is incurved in a concave manner and is of a material that is resiliently deformable during pressure of the jaws (7, 8).

13. Multifunctional clamp according to claim 12, wherein, the curvature of the two rear portions (17*a*, 17*b*) is symmetrical.

14. Multifunctional clamp according to claim 7, wherein, the distance between the distal end of the jaws (7, 8) and the pivot (6) is from 7 to 9 cm.

15. Multifunctional clamp according to claim 1, wherein, the jaws and gripping region are made of a plastic material.

16. Multifunctional clamp for medical use by a practitioner, comprising:

a practitioner gripping region (1); and two jaws (7, 8) pivotally articulated and controlled by the practitioner from the gripping region (1), each jaw (7, 8) comprising two parallel lengths of transversally oriented striations (13, 14) limited to internal jaw edge surfaces, in a direction of a longitudinal axis (15, 16) of the jaw (7, 8), the striations (13, 14) being complementary and interfiting when the jaws (7, 8) are brought together, a recess (11, 12) located within and intermediate the two lengths of the striations, the recesses (11, 12) having symmetrical openings with edges that contact with each other when the jaws (7, 8) are together, the recesses of the two jaws jointly defining a hollow volume when the jaws (7, 8) are brought together, and at least two claws (9, 10) at a distal end of each jaw, each claw oriented toward another claw (9, 10) and interfitting when the jaws are together, the striations being free of cutting edges and sharp extremity so as to enable the clamp to hold tissues without damage, and the claws are located only at the distal end, positioned to avoid cutting of the tissues.

17. Multifunctional clamp for medical use by a practitioner, comprising:

a practitioner gripping region (1); and two jaws (7, 8) pivotally articulated and controlled by the practitioner from the gripping region (1), each jaw (7, 8) comprising an internal surface crossing a width of the jaw, two parallel rows of transverse striations (13, 14) formed on edge portions of the internal surface, in a longitudinal axis direction of the jaw, the striations (13, 14) interfiting when brought together, the striations being free of cutting edges and sharp extremity, a recess (11, 12) located intermediate the two rows of the striations and surrounded by a portion of the the internal surface between the two rows of the striations, the recesses (11, 12) having symmetrical openings with edges that contact with each other when the jaws (7, 8) are brought together, the recesses of the two jaws jointly defining an enclosed hollow internal cavity when the jaws (7, 8) are brought together, and at least two claws (9, 10) at a distal end of each jaw, each claw oriented toward another claw (9, 10) and interfitting when the jaws are together, the claws located interior to an extension of each of the two rows of striations.

* * * * *